(12) United States Patent
Wang

(10) Patent No.: US 11,412,605 B2
(45) Date of Patent: Aug. 9, 2022

(54) PLASMA DEVICE INCLUDING TWO GAS INLETS

(71) Applicant: EverNew Biotech, Inc., Baoshan Township, Hsinchu County (TW)

(72) Inventor: Cheng-Nan Wang, Hsinchu County (TW)

(73) Assignee: EVERNEW BIOTECH, INC., Baoshan Township, Hsinchu County (TW)

( * ) Notice: Subject to any disclaimer, the term of this patent is extended or adjusted under 35 U.S.C. 154(b) by 274 days.

(21) Appl. No.: 16/910,283

(22) Filed: Jun. 24, 2020

(65) Prior Publication Data
US 2020/0404771 A1    Dec. 24, 2020

Related U.S. Application Data

(60) Provisional application No. 62/865,511, filed on Jun. 24, 2019.

(51) Int. Cl.
| | | |
|---|---|---|
| *H05H 1/24* | (2006.01) | |
| *H05H 1/46* | (2006.01) | |
| *H05H 1/34* | (2006.01) | |
| *A61N 1/44* | (2006.01) | |

(52) U.S. Cl.
CPC ............ *H05H 1/46* (2013.01); *H05H 1/34* (2013.01); *A61N 1/44* (2013.01); *H05H 1/466* (2021.05); *H05H 2245/36* (2021.05)

(58) Field of Classification Search
CPC ...... H05H 1/24; H05H 1/2406; H05H 1/2443; H05H 1/245; H05H 1/34; H05H 1/46
See application file for complete search history.

(56) References Cited

U.S. PATENT DOCUMENTS

| | | | | |
|---|---|---|---|---|
| 10,121,638 | B1 * | 11/2018 | Wu | H01J 37/32009 |
| 2001/0034519 | A1 * | 10/2001 | Goble | H05H 1/46 606/41 |
| 2012/0063966 | A1 * | 3/2012 | Liao | H05H 1/48 422/186 |
| 2015/0054405 | A1 * | 2/2015 | Nettesheim | H05H 1/36 315/111.21 |
| 2015/0340207 | A1 * | 11/2015 | Holbeche | H01J 37/32532 118/723 R |
| 2019/0209854 | A1 * | 7/2019 | Nagahara | A61C 19/06 |

* cited by examiner

*Primary Examiner* — Thai Pham
(74) *Attorney, Agent, or Firm* — Birch, Stewart, Kolasch & Birch, LLP

(57) ABSTRACT

Provided herein is a plasma generating device for medical treatment and sanitizing purposes which comprises a control unit and a plasma generator connecting to the control unit. The plasma generator comprises a plasma tube having a first end and a second end; a first dielectric layer disposed on the inner surface of the plasma tube; a first electrode disposed on the first dielectric layer; a second dielectric layer disposed on the first electrode; a second electrode disposed on the second dielectric layer; and a plasma nozzle disposed on the bottom cover on the second end of the plasma tube.

7 Claims, 6 Drawing Sheets

PLASMA DEVICE INCLUDING TWO GAS INLETS

CROSS REFERENCE

This Non-provisional application claims the priority under 35 U.S.C. § 119(a) on U.S. Patent Provisional Application No. 62/865,511 filed on Jun. 24, 2019, the entire contents of which are hereby incorporated by reference.

FIELD OF THE INVENTION

The present disclosure is related to a plasma device for inactivating microorganisms or viruses and helping microcirculation of blood; more particularly, to a plasma device including two gas inlets for inputting different gases.

BACKGROUND OF THE INVENTION

Atmospheric hot plasmas exist in natural phenomenon. Due to the high energy that plasma carries, it has been used in various applications including surface coating and display devices. Cold plasma processes are also known in the art. A positive to negative electrode configuration can generate cold plasma derived from various species of gases, e.g. atmospheric air or noble gases. As the temperature of cold atmospheric plasma is relatively low enough for human body treatments, a variety of plasma treatment methods have been reported in the prior art. A plasma treatment method must be able to effectively kill all kinds of organisms, including spores, without damaging the human bodies being treated.

The configuration of a plasma generator has to meet the parameters of the intended plasma treatment method, such as the input of the different species or combinations of gases, flow rate of the gases input, and the electrical energy applied to the gases. Furthermore, as the properties of plasma vary according to the different species or combinations of gases input, its therapeutic efficacy also varies. Prior arts, e.g. US 20110112522 A1 and US 10121638 B1, show the devices of plasma treatment comprising only one gas inlet. The device disclosed in prior art EP 2 160 081 A1 however requires one source of a gas being used as a carrier and at least another source of an additive which has a sterilizing effect and/or improves the healing of a wound and requires further a mixer to mix the carrier gas and the additive.

It is desirable and advisable to develop a plasma device that can use just one species of gas coming from one gas inlet at a given time for a particular treatment or different species of gases coming from two different gas inlets simultaneously to produce an intended combination of gases and generate such properties of plasma according to the gases input. With the configuration that can control and measure the gases input and generate plasma accordingly, plasma treatments for wound healing, sterilization and other intended purposes can then be improved.

SUMMARY OF THE INVENTION

The present invention comprises of a system, which can provide: (1) air, (2) a single non-corrosive gas, or (3) a combination of air and a non-corrosive gas.

The present invention is a device that utilizes direct cold atmospheric plasma to inactivate microorganisms or viruses and help microcirculation of blood. This device is for non-invasive medical treatment and aims to promote wound healing, alleviate pain, and decrease inflammation. This device can target both internal and external injuries.

This device can be applied for surface treatment purposes. This device also provides bactericidal and antiseptic benefits for surface cleaning, sterilization as well as personal or environmental hygiene and infection control particularly nosocomial infection or health care-associated infection.

The object of the present disclosure is to provide a device having two gas inlets, comprising: a control unit; a plasma generator connecting to the control unit. The control unit comprises: a first gas module; a second gas module; a total gas flow sensor; and a high voltage generator. The first gas module comprises: a first gas inlet and a first gas controller. The second gas module comprises: a second gas inlet and a second gas controller. The plasma generator comprises: a plasma tube having a first end and a second end; a first dielectric layer disposed on an inner surface of the plasma tube; a first electrode disposed on the first dielectric layer; a second dielectric layer disposed on the first electrode; a second electrode disposed on the second dielectric layer; and a plasma nozzle disposed on the second end of the plasma tube.

In a particular embodiment, wherein the plasma generator comprises the second electrode which is substantially in a shape of rotational symmetry.

In a particular embodiment, wherein the second electrode is in a round shape having a plurality of hollow cylinders inside.

In a particular embodiment, wherein the second electrode is in a round shape having a plurality of hollow leaflets inside.

In a particular embodiment, wherein the plasma generator further comprises a top cover and a bottom cover disposed on the first end and the second end respectively; the top cover connects to the control unit via a connector and the plasma nozzle is disposed on the bottom cover.

In a particular embodiment, wherein the control unit further comprises: a programmable logic controller (PLC); a buzzer; an AC/DC convertor; and a human machine interface (HMI).

In a particular embodiment, wherein the control unit connects to a power supply.

BRIEF DESCRIPTION OF THE DRAWINGS

The foregoing summary, as well as the following detailed descriptions of the invention, will be better understood when read in conjunction with the appended drawings. In the drawings.

DESCRIPTION OF THE INVENTION

The following embodiments when read with the accompanying drawings are made to clearly exhibit the abovementioned and other technical contents, features and effects of the present disclosure. Through the exposition by means of the specific embodiments, people would further understand the technical means and effects of the present disclosure adopted to achieve the above-indicated objectives. Moreover, as the contents disclosed herein can be readily understood and implemented by a person skilled in the art, all equivalent changes or modifications which do not depart from the concept of the present disclosure shall be encompassed by the appended claims.

Furthermore, the ordinals recited in the specification and the claims such as "first", "second" and so on are intended only to describe the elements claimed and imply or represent neither that the claimed elements have any proceeding ordinals, nor the sequence between one claimed element and another claimed element or between steps of a manufacturing method. The use of these ordinals is merely to differentiate one claimed element having a certain designation from another claimed element having the same designation.

Furthermore, the terms recited in the specifications and the claims such as "above", "over", or "on" are intended not only directly contact with the other element, but also intended indirectly contact with the other element.

The present disclosure is related to a device for medical treatment, hygiene, and sanitization purposes.

The device of the present disclosure is capable of utilizing direct cold atmospheric plasma to inactivate microorganisms or viruses, and ameliorate the microcirculation of blood. The device of the present disclosure aims to promote wound healing, alleviate pain, and decrease inflammation.

The device of the present disclosure provides bactericidal, virucidal, and antiseptic benefits for surface cleaning and sanitization as well as environmental hygiene purpose.

In one embodiment, the plasma generated by the device of the present disclosure is derived from air, non-corrosive gases, or the combination of both, in order to better meet the therapeutic efficacy and other demands delineated above. In a preferred embodiment, the plasma generated by the device of the present disclosure is derived from air, an inert gas, or the combination of both.

In one embodiment, the device of the present disclosure can be used on the body of animals and humans.

In one embodiment, the device of the present disclosure can target both internal and external injuries.

Figure 1:
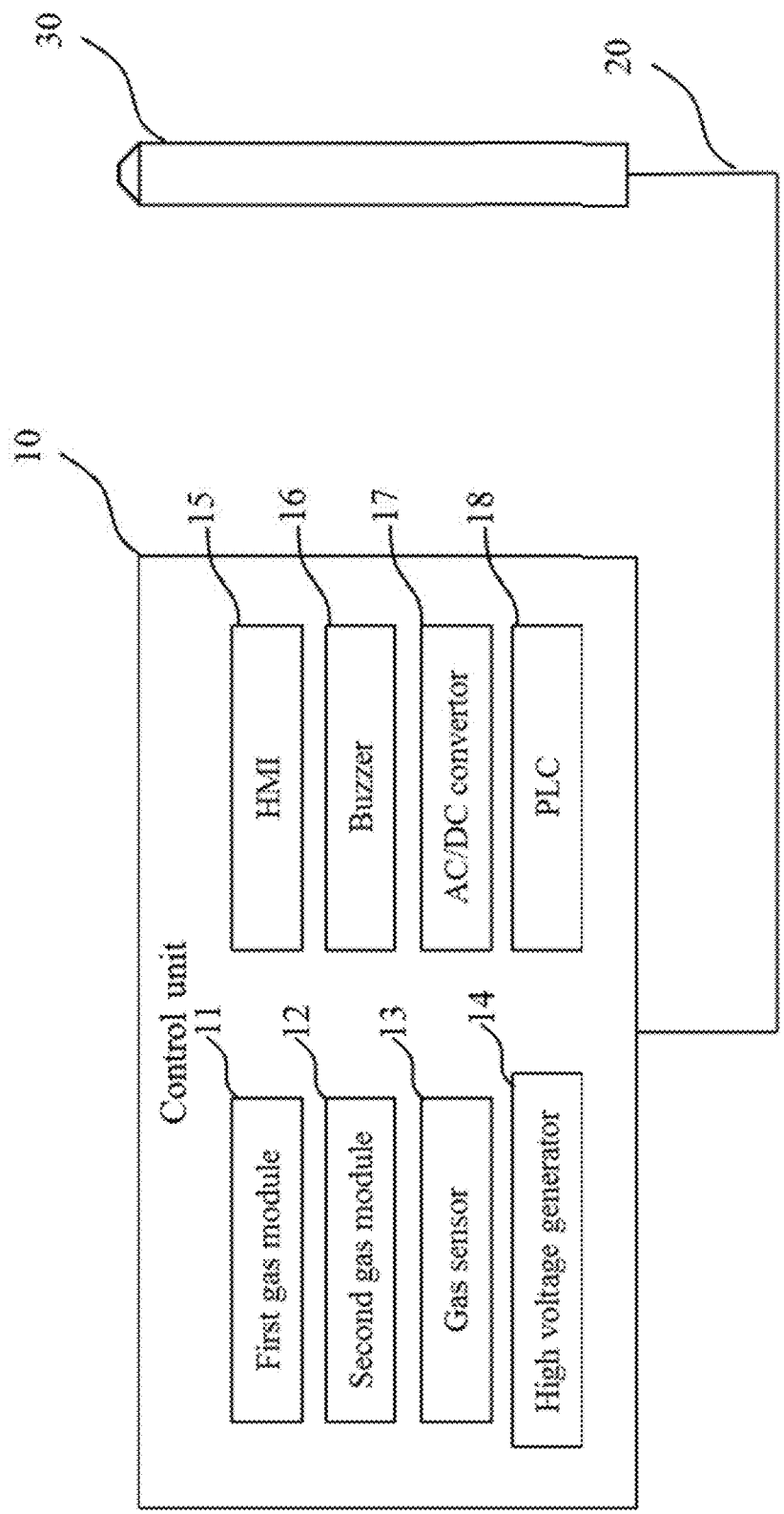
FIG. 1 shows the schematic view of the device of the present disclosure.

Please refer to FIG. 1. The device of the present disclosure comprises a control unit 10 and a plasma generator 30. The control unit 10 connects to the plasma generator 30 via a connector 20. The control unit 10 is disposed for the control of input of gas(es) and for the control of gas flow and power.

The control unit 10 comprises: a first gas module 11, a second gas module 12, a total gas flow sensor 13, and a high voltage generator 14.

In a particular embodiment, the control unit 10 further comprises a human machine interface (HMI) 15, a buzzer 16, an AC/DC convertor 17, and a programmable logic controller (PLC) 18.

Figure 2:
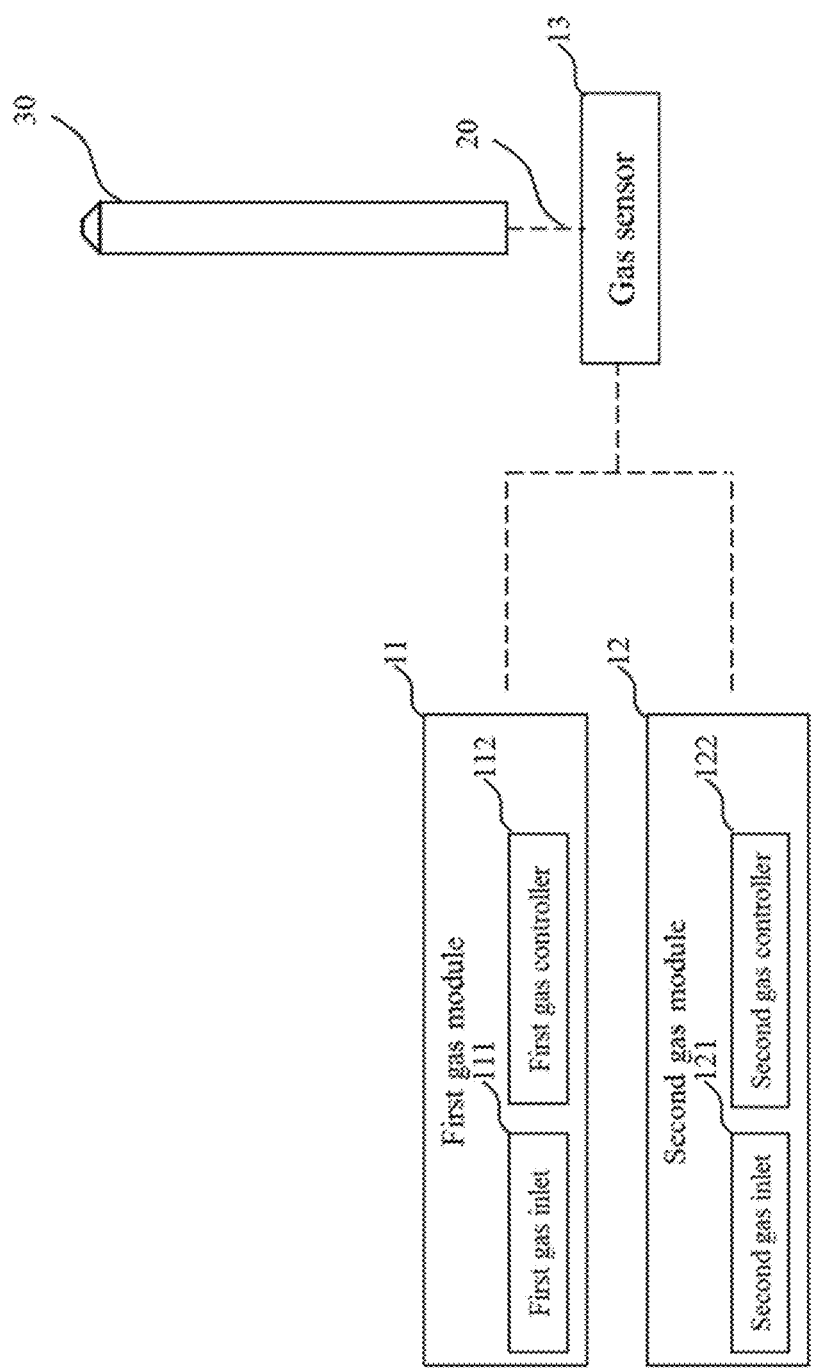
FIG. 2 shows the schematic view of the first and the second gas module of the device of the present disclosure.

Please refer to FIG. 2. The first gas module 11 comprises: a first gas inlet 111 and a first gas controller 112. The second gas module 12 comprises a second gas inlet 121 and a second gas controller 122. The gas modules 11, 12 input the gas (es) into the device of the present disclosure and transport the gas (es) to the plasma generator 30.

The gas inlets 111, 121 connect to different external gas cylinders (not shown in the figure). In one embodiment, the gas inlets 111, 121 are operated separately by the controllers 112, 122 respectively. In another particular embodiment, it can be chosen to open either one of the two gas inlets 111, 121 at a given time to input gas or to open both inlets 111, 121 simultaneously to input two different species of gases to make a combination of gases input.

The gas provided by the first gas inlet 111 and the one by the second gas inlet 121 are different. For example, air is input by gas inlet 111 and another species of non-corrosive gas is input by gas inlet 121. The gases provided by the gas inlets 111 and 121 can be a pure gas or a mixture of gases.

The two gas controllers 112 and 122 are disposed to control the input and the flow rate of the gas (es). The total gas flow sensor 13 is disposed to detect the flow rate of the gas (es) input.

The control unit 10 connects to a power supply to provide the electrical power to the device.

A programmable logic controller (PLC) 18 is disposed in the control unit 10 to control the functions and performances of the components of the device of the present disclosure. The components controlled by the PLC 18 include, but not limited to at least one of the followings: a countdown timer (not shown in the figure), gas controllers 112, 122, the total gas sensor 13, the high voltage power generator 14, the buzzer 16, and the main power on/off switch. In a particular embodiment, the PLC 18 operated by the on/off switch also controls the plasma generator 30 to begin or stop the plasma treatment.

The gas inlets 111, 121 can connect to different sources of gas to provide the device of the present disclosure to generate different properties of plasma. In a preferred embodiment, the gas input to the first gas inlet 111 is distinct to the gas input to the second gas inlet 121. The gases provided to the gas inlets 111, 121 are controlled and sensed by the gas controllers 112, 122.

In a particular embodiment, the gases provided via the gas inlets 111, 121 are merged into a single channel which supplies the gas to the plasma generator 30, and the merged gas flow is sensed by the total gas flow sensor 13.

In a particular embodiment in which different species of gas are used to generate plasma, the device of the present disclosure comprises a first gas module 11 and a second gas module 12, as shown in FIG. 1. However, in an alternative embodiment (not shown in the figure) in which only one species of gas is used to generate plasma, the device of the present disclosure comprises only one gas module.

Figure 3:
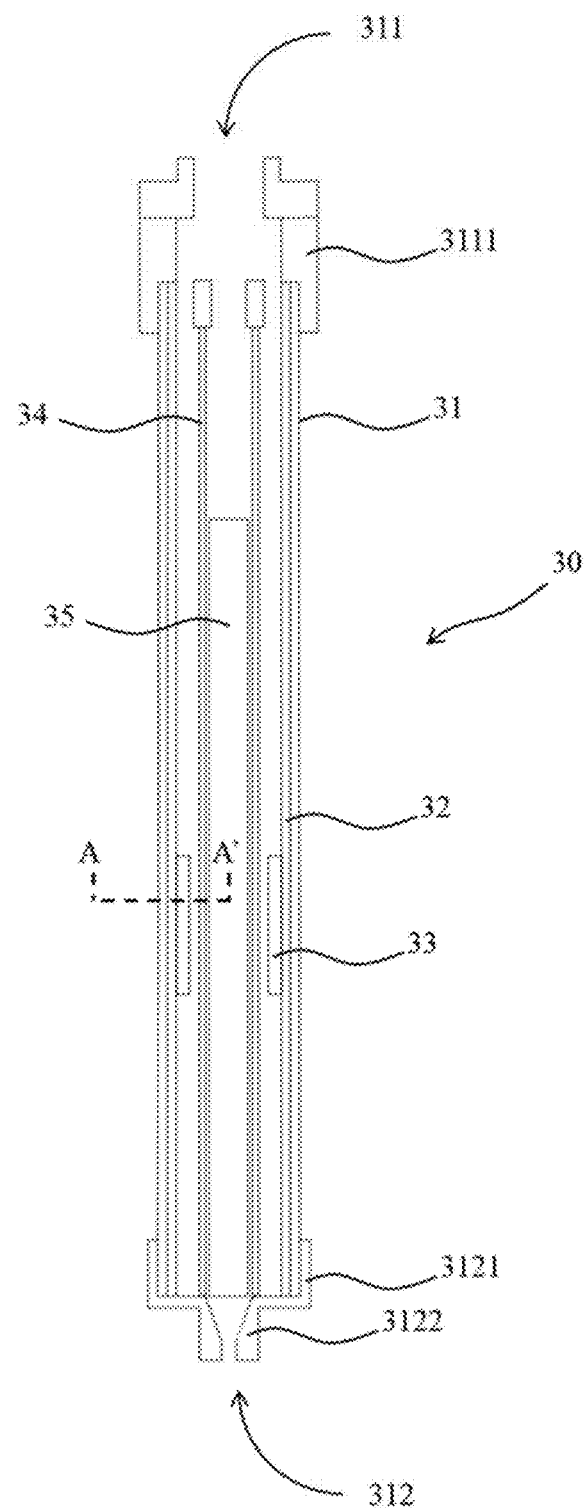
FIG. 3 shows the cross section view of the plasma generator of the device of the present disclosure.

Please refer to FIG. 3. The plasma generator 30 is preferably a round-shape tube in which the input gas and plasma generated flow through. The plasma generator 30 comprises a plasma tube 31 which has a first end 311 and a second end 312. The first end 311 of the plasma tube 31 connects to the control unit 10. A top cover 3111 is disposed on the first end 311, which is a head for a high voltage electrical current supply cable and external gas provided from the control unit 10 to go through. The top cover 3111 can be screwed on the plasma tube 31. A bottom cover 3121 is disposed on the second end 312. On the surface of the bottom cover 3121 there are locking means for disposable spacers and/or other accessories of different sizes and designs to be affixed to protect the bottom cover 3121, adjust the treatment area, and for hygiene purpose. The bottom cover 3121 can be screwed on the plasma tube 31.

A nozzle 3122 is disposed on the bottom cover 3121. The nozzle 3122 is the protruding part of the bottom cover 3121 and the diameter of the nozzle 3122 is in a range from 1 mm to 15 mm. In a preferred embodiment, the diameter of the nozzle 3122 is in a range from 1 mm to 10 mm. On the surface of the nozzle 3122 there are locking means for disposable spacers and/or other accessories of different sizes and designs to be affixed to protect the nozzle 3122, adjust the treatment area, and for hygiene purpose.

Figure 4:
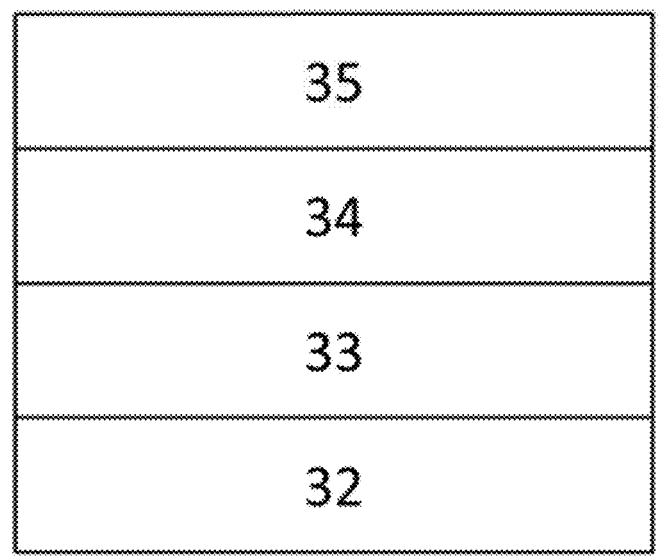
FIG. 4 shows another cross section view of a portion of the plasma generator of the device of the present disclosure.

Please refer to FIG. 4. FIG. 4 shows the cross-section view of a portion of the plasma generator 30 according to the A-A' line in FIG. 3.

The plasma tube 31 has an inner surface. A first dielectric layer 32 is disposed on the inner surface of the plasma tube 31. A first electrode 33 is disposed on the first dielectric layer 32. A second dielectric layer 34 is disposed on the first electrode 33. A second electrode 35 is disposed on the second dielectric layer 34. Although FIG. 4 shows that the dielectric layers are directly contact with the electrodes, the present disclosure is not limited hereto. The present disclosure also comprises the embodiment that the dielectric layers are indirectly contact with the electrodes, as shown in FIG. 3.

It should be noticed that although FIG. 4 demonstrates that the second dielectric layer 34 is disposed on the first electrode 33, in an alternative embodiment according to FIG. 3, the second dielectric layer 34 partially overlaps with the first electrode 33 and partially faces the first dielectric layer 32. Thus, in an alternative embodiment of the present disclosure, the dielectric layers and the electrodes partially overlap. In a particular embodiment, the first electrode 33 is cathode and the second electrode 35 is anode.

Figure 5:
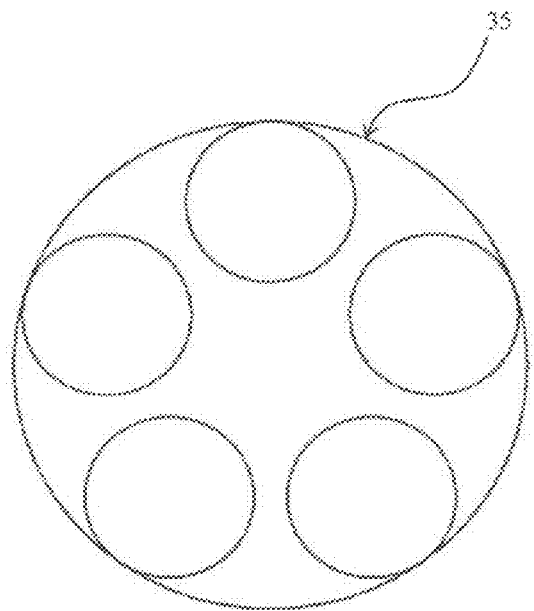
FIG. 5(A) and FIG. 5(B) show top views of the second electrode in alternative embodiments (other components omitted).
Figure 5:
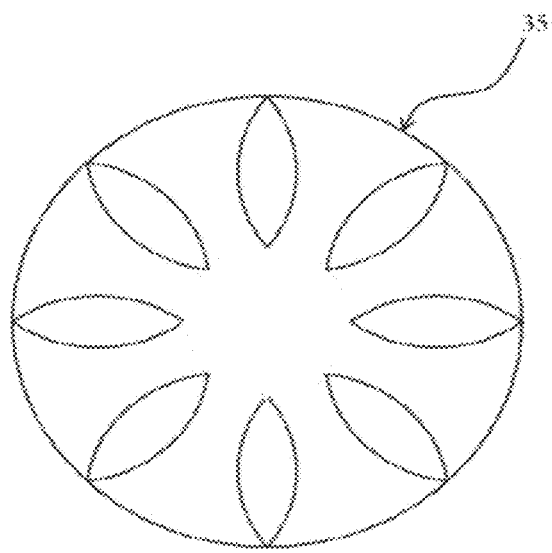

FIG. 5 discloses a top view of the second electrode 35 (other components omitted). The second electrode 35 is disposed in the center of the plasma generator 30 and is in a shape of rotational symmetry.

In one embodiment, the second electrode 35 is in a round shape which comprises a plurality of hollow cylinders inside as shown in FIG. 5(A). In an alternative embodiment, the second electrode 35 is in a round shape which has a plurality of hollow tubes in the shape of a leaflet inside, as shown in FIG. 5(B).

However, the number of cylinders or leaflets of the second electrode 35 is not limited to the number as shown in the figures. The number of cylinders or leaflets in the second electrode 35 can be in a range between 1 and any number that fits.

The device of the present disclosure is tested on a wet solid medium on agar plate which is inoculated with microorganism.

The experiment is conducted via a time-dependent and localized spot-like plasma treatment using the device of the present disclosure on the inoculated plate, towards the point of target microorganism without moving the nozzle of the device.

The protocol of experiment includes the following steps:
1. Selecting a single colony from a TSB plate in which microbes grow, subculturing the same in a 5 ml tube including TSB medium, and incubating the microbes in shaking incubators under 30° C. for 14-24 hours;
2. Taking 100 µl culture medium and diluting 10×, and then detecting $OD_{600}$ by a spectrometer (1 OD=$1\times10^9$ cfu/ml);
3. Conducting serial dilution with water to dilute the concentration of microbe to $10^5$ ($8.67\times10^5$ cfu/ml);
4. Taking 500 µl diluted microbe ($10^5$) and culturing the same on a TSB plate;
5. Treating the microbe on the plate with the plasma generated by the device of the present disclosure; the distance between the opening of the nozzle and plate is 5 mm;
6. Incubating the microbe under 30° C. for 1-2 days and observing the growth inhibition zone.

The growth inhibition zone of the microorganism is defined as circular area without visible growth of *E. coli*.

The experiment was conducted according to the designs of the followings, with air and Argon provided to generate plasma:

| | Suitable Medium | Incubation Temperature | Inoculum Incubation Time | Microbial Recovery Incubation Time | |
|---|---|---|---|---|---|
| *Escherichia coli* (BCRC 16081) | TSB | 30° C. | 14 to 24 hours | 1 to 2 days | 1 OD = $1 \times 10^9$ cfu/ml |

The plasma treatment varies according to the protocol of treatment, such as the species of gas, treatment time, and the distance between the opening of the nozzle and the plate.

Figure 6:
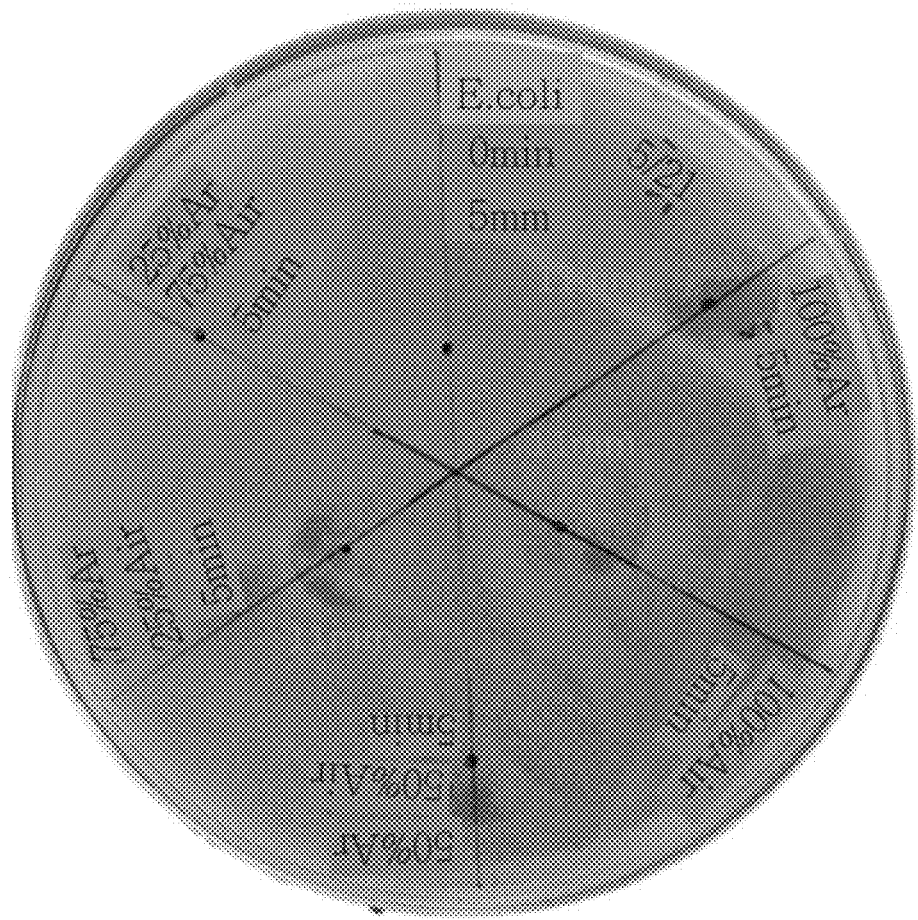
FIG. 6 shows the results of plasma treatments on agar plates inoculated with Escherichia coli (*E. coli*) and the growth inhibition zones thereof.

The microbes on the plate were treated by different ratio of air and argon, as shown in FIG. 6.

As shown in FIG. 6, the treatment with 100% argon, 100% air, and 75% argon and 25% air each would contribute to a growth inhibition zone with a diameter of 11 mm.

While preferred embodiments of the present invention have been shown and described herein, it will be obvious to those skilled in the art that such embodiments are provided by way of example only and can be implemented in combinations. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:
1. A device including two gas inlets, comprising:
   a control unit, comprising:
      a first gas module, comprising:
         a first gas inlet; and
         a first gas controller;
      a second gas module, comprising:
         a second gas inlet; and
         a second gas controller;
      a total gas flow sensor; and
      a high voltage generator;
   a plasma generator, connecting to the control unit and comprising:
      a plasma tube having a first end and a second end;
      a first dielectric layer disposed on the inner surface of the plasma tube;
      a first electrode disposed on the first dielectric layer;
      a second dielectric layer disposed on the first electrode;
      a second electrode disposed on the second dielectric layer; and
      a plasma nozzle disposed on the second end of the plasma tube.

2. The device of claim 1, wherein the plasma generator comprises the second electrode which is substantially in a shape of rotational symmetry.

3. The device of claim 2, wherein the second electrode is in a round shape having a plurality of hollow cylinders inside.

4. The device of claim 2, wherein the second electrode is in a round shape having a plurality of hollow tubes in the shape of a leaflet inside.

5. The device of claim 1, wherein the plasma generator further comprises a top cover and a bottom cover disposed on the first end and the second end respectively; the top cover connects to the control unit via a connector and the plasma nozzle is disposed on the bottom cover.

6. The device of claim 5, wherein the control unit further comprises: a programmable logic controller (PLC); a buzzer; an AC/DC convertor; and a human machine interface (HMI).

7. The device of claim 1, wherein the control unit connects to a power supply.

* * * * *